United States Patent [19]

Dekeyser et al.

[11] Patent Number: 5,438,123
[45] Date of Patent: Aug. 1, 1995

[54] INSECTICIDAL PHENYLHYDRAZINE DERIVATIVES

[75] Inventors: Mark A. Dekeyser, Waterloo, Canada; Paul T. McDonald, Middlebury, Conn.

[73] Assignees: Uniroyal Chemical Company, Inc., Middlebury, Conn.; Uniroyal Chemical Ltd./Ltee, Elmira, Canada

[21] Appl. No.: 286,738

[22] Filed: Aug. 5, 1994

Related U.S. Application Data

[60] Division of Ser. No. 979,095, Nov. 10, 1992, Pat. No. 5,367,093, which is a continuation-in-part of Ser. No. 796,506, Nov. 22, 1991, abandoned.

[51] Int. Cl.⁶ .................. C07C 245/06; A01N 37/30
[52] U.S. Cl. .................... 534/885; 514/150
[58] Field of Search .................. 534/885; 514/150

[56] References Cited

U.S. PATENT DOCUMENTS

| | | | |
|---|---|---|---|
| 4,006,132 | 2/1977 | Moon | 260/192 |
| 4,558,040 | 12/1985 | Pilgram et al. | 514/150 |
| 4,638,088 | 1/1987 | Chou et al. | 564/23 |
| 5,089,486 | 2/1992 | Wood et al. | 514/149 |
| 5,387,580 | 2/1995 | Wood et al. | 514/150 |

OTHER PUBLICATIONS

Smissman et al., J. Org. Chem., vol. 37, No. 11, pp. 1704–1707 (1972).

Primary Examiner—José G. Dees
Assistant Examiner—Barbara S. Frazier
Attorney, Agent, or Firm—Daniel Reitenbach

[57] ABSTRACT

Compounds having the structural formula

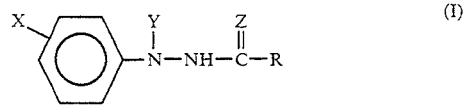

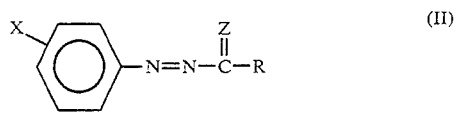

where X, Y, R and Z are defined in the specification are disclosed. The compounds of this invention are effective for controlling mites, nematodes, rice planthopper, tobacco budworm, and southern corn rootworm. Methods for making these compounds are also set forth.

4 Claims, No Drawings

INSECTICIDAL PHENYLHYDRAZINE DERIVATIVES

CROSS REFERENCE TO RELATED APPLICATION

This is a division of application Ser. No. 07/979,095, filed Nov. 10, 1992, now U.S. Pat. No. 5,367,093, which is a continuation-in-part of application Ser. No. 07/796,506, filed Nov. 22, 1991, now abandoned.

BACKGROUND OF THE INVENTION

1. Field of the Invention

This invention is directed to novel phenylhydrazine derivatives which exhibit activity as insecticides, acaricides and nematicides. This invention is also directed to insecticidal, acaricidal or nematicidal compositions comprising such compounds as well as to methods of controlling insects, acarids and nematodes employing such compounds or compositions.

Destruction by insects, acarids and nematodes presents a serious problem to agriculture. A wide variety of field crops are in need of protection from nematodes, acarids, and insects including such valuable crops as soybeans, corn, peanuts, cotton, alfalfa, rice and tobacco. In addition, vegetables, such as tomatoes, potatoes, sugarbeet, carrots, peas, and the like as well as fruits, nuts, ornamentals and seed bed crops such as apples, peaches, almonds, citrus fruit and grapes may also require protection from the ravages of such pests.

Consequently, the development of new, more effective pesticides including insecticides, acaricides and nematicides represents an ongoing scientific activity. More particularly, the development of pesticides which are effective as both ovicides and larvicides are of interest.

2. Description of Related Art

Chemical Abstracts 108(19):163280d refers to alkyl phenylhydrazinecarboxylates said to be useful as acaricides. U.S. Pat. No. 4,725,302 refers to substituted phenylhydrazines and phenyloxadiazolinones said to be useful as pesticides. European Patent 0 067 471 refers to 7-substituted 2,3-dihydrobenzofurans said to be useful as pesticides or chemical intermediates. DerWent abstract 88-312695/44 refers to arylhydrazides of trifluoroacetic acid said to have fungicidal, bacteriocidal, acaricidal, and antiseptic activity. Chemical Abstracts 105(17):152686c refers to various phenylhydrazines said to have activity against insects and mites.

SUMMARY OF THE INVENTION

The instant invention relates to a compound having the structural formula (I) or (II):

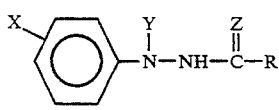 (I)

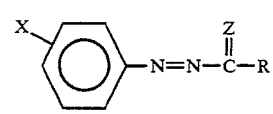 (II)

wherein:

X is a) phenyl; lower phenylalkoxy; phenoxy; or benzyl; or b) one substituent from group a) and one or more substituents selected from $C_1$–$C_4$ alkoxy; halogen; lower alkyl; and lower alkylthio; or c) along with the phenyl to which it is attached, forms a multiple fused ring heterocycle such as dibenzofuranyl;

Y is H, $C_1$–$C_4$ alkanoyl, $C_1$–$C_4$ haloalkanoyl, dialkoxyphosphoryl, alkylaminocarbonyl, haloalkylsulfonyl, or $C_1$–$C_4$ alkoxy carbonyl; and R is H, $C_1$–$C_6$ alkyl, $C_1$–$C_6$ alkoxy, $C_3$–$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, or $C_3$–$C_6$ cycloalkyl; and Z is O or S.

Further, when X includes a substituent having a phenyl ring (i.e., is phenyl, phenylalkoxy, phenoxy or benzyl), the phenyl ring is optionally substituted with one or more of halogen, nitro, lower alkyl, lower alkoxy, lower haloalkyl, or dialkylamino.

The instant invention further relates to pesticidal compositions comprising:

a) an effective amount of a compound having the structure of formula (I) or (II) above as an active ingredient; and (b) an agriculturally acceptable carrier.

The present invention is also directed to a method for controlling pests such as insects, acarids or nematodes which comprises applying an effective amount of a compound of formula (I) or (II) or of a composition of the present invention to a locus to be protected or rid of pests.

DETAILED DESCRIPTION OF THE INVENTION

The compounds of the present invention have the structure (I) or (II) defined above. Preferred compounds are those in which Y is hydrogen or COCF$_3$.

The compounds having structure (I) may be prepared by reacting a substituted phenylhydrazine:

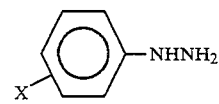

with an acylating agent:

wherein Z is halo or

and an equivalent of an HCl acceptor such as pyridine in a solvent such as toluene. The product of this reaction may be further acylated, or converted by oxidation with an oxidizing agent such as Pd/air to form compounds having structure (II).

The compositions of this invention comprise (a) a compound having a structure within that of formula (I) or (II) above, and (b) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of tile resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To combat pests, sprays of the compounds may be applied to the pests directly and/or to plants upon which they feed or nest. The pesticidally active formulations may also be applied to the soil or other medium in which the pests are present.

Harmful insects, nematodes and acarids attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as insecticides, nematicides and acaricides, for foliar and/or soil application.

EXAMPLES

The following Examples are intended to further illustrate the invention, and are not intended to limit the scope of the invention in any manner whatsoever.

EXAMPLE 1

Preparation of (4-methoxy-[1,1'-biphenyl]-3-yl)hydrazine hydrochloride (chemical intermediate)

To 25 g of 5-phenyl-o-anisidine were added 250 ml of water and 450 ml of concentrated hydrochloric acid and the stirred solution was cooled to 0° C. A solution of 8.6 g of sodium nitrite in 20 ml of water was then added dropwise, maintaining a temperature of 0° C. After this addition the mixture was stirred, at 0° C. for 1 hour. A solution of 113 g of stannous chloride in 200 ml of concentrated HCl, cooled to −20° C., was added to the reaction mixture and again the mixture was stirred for one hour. The mixture was then suction filtered and the resulting solid was allowed to dry overnight. The solid was dissolved in hot water, gravity filtered, and the filtrate cooled on ice. The crystallized solid was then suction filtered and the product was allowed to dry overnight. The product obtained was 26 g of (4-methoxy-[1,1'-biphenyl]-3-yl)hydrazine hydrochloride.

EXAMPLE 2

Preparation of 2-(4-methoxy-[1,2'-biphenyl]-3-yl)hydrazide of propanoic acid (Compound 18)

To 5 g of the product of Example 1 was added 100 ml of water and 40 ml of 10% sodium hydroxide solution and the mixture was allowed to stir for 1 hour at room temperature. The mixture was then extracted with ether and the ether extract was dried over sodium sulfate for one half hour. The ether extract was then filtered and evaporated under reduced pressure to yield 4.6 g of the intermediate, (4-methoxy-[1,1'-biphenyl]-3-yl)hydrazine.

To 4.6 g of the above intermediate, 150 ml of toluene and 1.58 g of pyridine were added and the solution was stirred and cooled to 0° C. Then, 1.84 g of propionyl chloride was added dropwise. After addition of the propionyl chloride, the solution was stirred for 1 hour at 0° C. The solution was then washed twice, each time with 100 ml of water. The water fraction was saved and extracted with toluene. The toluene fractions from the extraction were combined and evaporated under reduced pressure. The resulting solid was washed with hexane and filtered. The product obtained was 3.4 g of 2-(4-methoxy-[1,1'-biphenyl]-3-yl)hydrazide of propanoic acid.

EXAMPLE 3

Preparation of 2-(4-methoxy-[1,1'-biphenyl]-3-yl)-2-(trifluoroacetyl)hydrazide of propanoic acid (Compound 73)

To 2.25 g of the product of Example 2 was added 150 ml of methylene chloride. The solution was stirred and cooled to 0° C. Then 1.75 g of trifluoroacetic anhydride was added dropwise, the flask stoppered, and the reaction stirred overnight. The solvent was then evaporated under reduced pressure to yield a solid which was washed with hexane and filtered. The final product obtained was 2.7 g of 2-(4-methoxy-[1.1'-biphenyl]-3-yl)-2-(trifluoroacetyl)hydrazide of propanoic acid, with a melting point of 126° C.

EXAMPLE 4

Preparation of (4-bromo-[1,1'-biphenyl]-3-yl)hydrazine hydrochloride (chemical intermediate)

To 4 g of 4-bromo-[1,1'-biphenyl]-3-amine were added 25 ml of water and 50 ml of concentrated HCl with stirring. The solution was cooled to 0° C. A solution of 1.1 g of sodium nitrite in 6 ml of water was then added dropwise while maintaining a temperature of 0° C. After this addition, the mixture was stirred at 0° C. for one hour. A solution of 20 g of stannous chloride in 20 ml of concentrated HCl cooled to −20° C. was added to the reaction mixture and again the mixture was stirred for one hour.

The precipitate was then suction filtered and the resulting solid was allowed to dry overnight. The product, (4-bromo-[1,1'-biphenyl]hydrazine hydrochloride, was used in subsequent reactions without further purification.

EXAMPLE 5

Preparation of isopropyl 2-(4-bromo-[1,1'-biphenyl]-3-yl) hydrazine carboxylate (Compound 139)

To the product of Example 4 was added 100 ml of a 10% aqueous sodium hydroxide solution and the mixture was stirred for 30 minutes at 10° C. The mixture was then extracted with ether, dried over sodium sulfate for 2 hours, and evaporated, leaving 3 g of (4-bromo-[1,1'-biphenyl]-3-yl)hydrazine. To 3 g of the hydrazine were added 100 ml of toluene and 1.5 g of pyridine and the resulting mixture was cooled an ice bath. Twelve ml of a 1M solution of isopropyl chloroformate in toluene were added dropwise. After the addition of isopropyl chloroformate, the solution was allowed to stir overnight at room temperature. The solution was then washed twice, each time with 100 ml of water, dried over sodium sulfate for 2 hours, and evaporated under reduced pressure.

The resulting solid was washed with hexane and recrystallized from toluene. The product obtained was 3 g of isopropyl 2-(4-bromo-[1,1'-biphenyl]-3-yl) hydrazinecarboxylate with melting point 107°–108° C.

EXAMPLE 6

Preparation of isopropyl (4-bromo-[1,1'-biphenyl]-3-yl) diazenecarboxylate (Compound 161)

To 1.7 g of the product of Example 4 was added 100 ml of toluene and 0.4 g of palladium on charcoal. The mixture was stirred overnight at room temperature, then filtered out and the toluene evaporated under reduced pressure. The product obtained was 1.5 g of isopropyl (4-bromo-[1,1'-biphenyl]-3-yl)diazene carboxylate as a red oil.

EXAMPLE 7

Preparation of 2-methoxy-3-dibenzofuranyl hydrazine (chemical intermediate)

To 10 g of 3-amino-2-methoxydibenzofuran were added 100 ml of water and 50 ml of concentrated HCl with stirring. The solution was cooled to 0° C. A solution of 3.5 g of sodium nitrite in 15 ml of water was then added dropwise, maintaining a temperature of 0° C. After this addition, the mixture was stirred at 0° C. for one hour. A solution of 40 g of stannous chloride in 50 ml of concentrated HCl cooled to −20° C. was added to the reaction mixture and the mixture was stirred for one hour.

The precipitate was then suction filtered and the resulting solid added to a solution of 70 g sodium hydroxide in 500 ml of water cooled in an ice bath. The mixture was then extracted with ether, dried over sodium sulfate for 2 hours, and evaporated to a solid. The solid was washed with hexane, leaving 7 g of 2-methoxy-3-dibenzofuranyl hydrazine of mp 113°–115° C.

EXAMPLE 8

Preparation of isopropyl 2-(2-methoxy-3-dibenzofuranyl) hydrazinecarboxylate (Compound 141)

To 2.3 g of the product of Example 7 were added 100 ml of toluene and 1 g of pyridine and the resulting mixture was cooled in an ice bath. Ten ml of a 1M solution of isopropyl chloroformate in toluene was then added dropwise. After this addition, the solution was allowed to stir overnight at room temperature.

The solution was then washed twice, each time with 100 ml of water, dried over sodium sulfate for two hours, and then evaporated under reduced pressure. The resulting solid was washed with hexane and recrystallized from toluene. The product obtained was 2 g of isopropyl 2-(2-methoxy-3-dibenzofuranyl) hydrazine carboxylate with mp of 178° C.

EXAMPLE 9

Preparation of isopropyl (2-methoxy-3-dibenzofuranyl) diazenecarboxylate (Compound 157)

To 1.4 g of the product of Example 7 were added 100 ml of toluene and 0.3 g of palladium on charcoal. The mixture was stirred overnight at room temperature, filtered, and the toluene evaporated under reduced pressure. The product obtained was 1.2 g of isopropyl (2-methoxy-3-dibenzofuranyl) diazenecarboxylate as a red oil.

The compounds summarized in Tables 1–4B and numbered from 1–161 were prepared using essentially the same processes as shown in the foregoing examples. Where starting compounds were not commercially available, they were synthesized by methods well known in the art. Each of the compounds so formed is characterized by their NMR characteristics.

TABLE 1

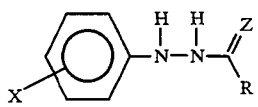

| COMPOUND | X | R | Z | NMR DATA FOR NOTES 1 (CDCL$_3$) |
|---|---|---|---|---|
| 1 | 2-C$_6$H$_5$ | CH$_3$ | O | s(3)1.9; m(10)6.8–7.5; bs(1)9.9 |
| 2 | 2-C$_6$H$_5$ | OCH$_3$ | O | s(3)3.6; s(1)6.5; m(9)6.8–7.5; bs(1)9.1 |
| 3 | 2-C$_6$H$_5$ | OCH$_2$CH$_3$ | O | t(3)1.2; q(2)4.0; s(1)6.5; m(9)6.7–7.5; bs(1)9.0 |
| 4 | 2-C$_6$H$_5$ | C(CH$_3$)$_3$ | O | s(9)1.2; m(10)6.8–7.5; bs(1)9.7 |
| 5 | 2-C$_6$H$_5$ | C$_5$H$_9$-c | O | m(8)1.4–1.8; m(1)2.4–2.8; d(1)6.5; m(9)6.7–7.5; d(1)9.8 |
| 6 | 2-C$_6$H$_5$ | OCH$_2$C$_6$H$_5$ | O | s(2)5.1; s(1)6.5; m(14)6.8–7.5; s(1)9.8 |
| 7 | 2-C$_6$H$_5$ | OCH(CH$_3$)$_2$ | O | d(6)1.2; m(1)4.9; bs(1)5.9; bs(1)6.3; m(9)6.8–7.5 |
| 8 | 3-C$_6$H$_5$ | CH$_3$ | O | s(3)2.0; m(9)6.8–7.5; bs(1)8.7; bs(1)9.7 |
| 9 | 2-CH$_3$O, 5-C$_6$H$_5$ | CH$_2$Cl | O | s(3)3.8; s(2)3.9; m(9)6.9–7.6; bs(1)9.8 |
| 10 | 2-CH$_3$O, 5-C$_6$H$_5$ | OCH$_3$ | O | s(3)3.7; s(3)3.8; bs(1)6.2; m(9)6.7–7.5 |
| 11 | 2-CH$_3$O, 5-C$_6$H$_5$ | OCH$_2$CH$_3$ | O | t(3)1.2; s(3)3.8; q(2)4.2; bs(1)6.3; bs(1)6.4; m(8)6.7–7.5 |
| 12 | 2-CH$_3$O, 5-C$_6$H$_5$ | CH$_2$CH$_2$CH$_3$ | O | t(3)0.9; m(2)1.5; t(2)2.2; s(3)3.8; m(9)6.8–7.5; d(1)9.8 |
| 13 | 2-CH$_3$O, 5-C$_6$H$_5$ | CH(CH$_3$)$_2$ | O | d(6)0.9; m(1)2.9; s(3)3.8; m(9)6.8–7.5 bs(1)9.8 |
| 14 | 2-CH$_3$O, 5-C$_6$H$_5$ | C(CH$_3$)$_3$ | O | s(9)1.1; s(3)3.8; m(9)6.8–7.5; bs(1)9.8 |
| 15 | 2-CH$_3$O, 5-C$_6$H$_5$ | OCH$_2$C$_6$H$_5$ | O | s(3)3.9; s(2)5.0; m(2)6.4; m(8)6.9–7.6 |
| 16 | 2-CH$_3$O, 5-C$_6$H$_5$ | CH$_2$OCH$_3$ | O | s(3)3.3; s(3)3.8; s(2)4.0; bs(1)6.5; m(8)6.7–7.5; bs(1)8.3 |
| 17 | 2-CH$_3$O, 5-C$_6$H$_5$ | C(CH$_3$)=CH$_2$ | O | s(3)2.0; s(3)3.8; s(1)5.2; s(1)5.7; bs(1)6.5; m(8)6.7–7.5; bs(1)8.3 |
| 18 | 2-CH$_3$O, 5-C$_6$H$_5$ | CH$_2$CH$_3$ | O | t(3)1.2; q(2)2.3; s(3)3.8; bs(1)6.5; m(8)6.8–7.5; bs(1)8.3 |
| 19 | 2-CH$_3$O, 5-C$_6$H$_5$ | O(CH$_2$)$_3$CH$_3$ | O | t(3)0.9; m(4)1.5; s(3)3.8; t(2)4.1; bs(1)6.5; m(8)6.8–7.5 |
| 20 | 2-CH$_3$O, 5-C$_6$H$_5$ | OCH$_2$CH$_2$CH$_3$ | O | t(3)0.9; m(2)1.6; s(3)3.8; t(2)4.1; bs(1)6.3; bs(1)6.5; m(8)6.8–7.5 |
| 21 | 2-CH$_3$O, 5-C$_6$H$_5$ | OCH$_2$CH(CH$_3$)$_2$ | O | d(6)0.9; m(1)1.9; s(3)3.8; d(2)3.9; bs(1)6.3; bs(1)6.6; m(8)6.8–7.5 |
| 22 | 2-CH$_3$O, 5-C$_6$H$_5$ | NHC$_3$H$_7$ | S | t(3)1.0; m(2)1.7; q(2)3.6; s(3)3.9; s(1)6.5; m(9)6.8–7.5; s(1)8.5 |
| 23 | 2-CH$_3$O, 5-C$_6$H$_5$ | CO$_2$CH$_2$CH$_3$ | O | t(3)1.2; s(3)3.8; q(2)4.2; m(8)6.8–7.5; bs(1)8.3; bs(1)9.8 |
| 24 | 2-CH$_3$O, 5-C$_6$H$_5$ | SCH$_2$CH$_3$ | O | t(3)1.2; q(2)2.7; s(3)3.8; m(9)6.8–7.5; bs(1)9.5 |
| 25 | 2-CH$_3$O, 5-C$_6$H$_5$ | OCH$_2$CH=CH$_2$ | O | s(3)3.8; d(2)4.6; m(3)5.1–6.0; bs(1)6.3; bs(1)6.5; m(8)6.8–7.5 |
| 26 | 2-CH$_3$O, 5-C$_6$H$_5$ | OCH(CH$_3$)$_2$ | O | d(6)1.2; s(3)3.8; m(1)5.0; bs(1)6.3; bs(1)6.5; m(8)6.8–7.5 |
| 27 | 2-CH$_3$O, 5-C$_6$H$_5$ | CH$_2$C(CH$_3$)$_3$ | O | s(9)1.0; s(2)2.1; s(3)3.8; bs(1)6.5; m(8)6.8–7.5 |
| 28 | 2-CH$_3$O, 5-C$_6$H$_5$ | CF$_2$CF$_3$ | O | s(3)3.8; m(8)6.8–7.5; bs(2)8.2 |
| 29 | 2-CH$_3$O, 5-C$_6$H$_5$ | CF$_2$Cl | O | s(3)3.8; bs(1)6.0; m(8)6.8–7.5; bs(1)8.2 |
| 30 | 2-CH$_3$O, 5-C$_6$H$_5$ | 2-C$_4$H$_3$S | O | s(3)3.8; m(13)6.7–7.9 |
| 31 | 2-C$_6$H$_5$ | H | O | m(10)6.7–7.5; bs(1)8.1; bs(1)9.9; |
| 32 | 2-C$_6$H$_5$ | CF$_3$ | O | m(11)6.7–7.5 |
| 33 | 2-CH$_3$O, 5-C$_6$H$_5$ | H | O | s(3)3.9; m(9)6.9–7.7; bs(1)8.1; bs(1)9.8 |
| 34 | 2-CH$_3$O, 5-C$_6$H$_5$ | CH$_3$ | O | s(3)2.0; s(3)3.8; m(10)6.8–7.7 |
| 35 | 2-CH$_3$O, 5-C$_6$H$_5$ | CF$_3$ | O | s(3)3.8; m(10)6.8–7.7 |
| 36 | 2-CH$_3$O, 5-C$_6$H$_5$ | CHClCH$_3$ | O | d(3)1.5; s(3)3.9; q(1) |
| 37 | 2-CH$_3$O, 5-C$_6$H$_5$ | CH$_2$C$_6$H$_5$ | O | s(2)3.5; s(3)3.9; m(15)5.8–7.4 |
| 38 | 2-CH$_3$O, 5-C$_6$H$_5$ | cyclohexyl | O | m(11)1.1–1.8; s(3)3.8; m(9)6.8–7.5; bs(1)9.8 |
| 39 | 2-CH$_3$O, 5-C$_6$H$_5$ | OCH$_2$CH$_2$OCH$_3$ | O | s(3)3.3; t(2)3.5; s(3)3.8; t(2)4.2; bs(1)6.3; m(8)6.8–7.5 |
| 40 | 2-CH$_3$O, 5-C$_6$H$_5$ | OCHClCH$_3$ | O | d(3)1.8; s(3)3.8; m(1)6.5; m(10)6.8–7.6 |
| 41 | 2-CH$_3$O, 5-C$_6$H$_5$ | OC$_6$H$_5$ | O | s(3)3.8; m(15)6.5–7.8 |
| 42 | 2-C$_6$H$_5$ | OC$_3$H$_7$ | O | m(5)0.8–1.7; m(2)4.1; bs(1)5.9 m(10)6.7–7.5 |
| 43 | 2-C$_6$H$_5$ | OCH$_4$H$_9$ | O | m(7)0.8–1.7; m(2)4.1; bs(1)5.9 m(10)6.7–7.6 |
| 44 | 2-CH$_3$O, 5-C$_6$H$_5$ | OCH=CH$_2$ | O | s(3)3.8; m(2)4.5–5.0 bs(1)6.2; m(10)6.7–7.6 |
| 45 | 2-CH$_3$O, 5-C$_6$H$_5$ | OC(CH$_3$)$_2$CCl$_3$ | O | s(6)1.9; s(3)3.9; bs(1)6.2; m(9)6.8–7.6 |
| 46 | 2-CH$_3$O, 5-C$_6$H$_5$ | O-cyclohexyl-3-Cl | O | m(8)1.0–2.2; s(3)3.9; m(10)6.5–7.5 |
| 47 | 2-CH$_3$O, 5-C$_6$H$_5$ | OCH$_2$CH$_2$Cl | O | m(2)3.6; s(3)3.8; m(2)4.3; bs(1)6.2 m(9)6.7–7.6 |
| 48 | 2-CH$_3$O, 5-C$_6$H$_5$ | CCl$_3$ | O | s(3)3.9; m(10)6.8–7.8 |
| 49 | 2-CH$_3$O, 5-C$_6$H$_5$ | OCH$_2$CH=CH$_2$ | O | d(2)4.5; m(3)5.0–6.0; m(11)6.7–7.6 |
| 50 | 3-C$_6$H$_5$ | OCH(CH$_3$)$_2$ | O | d(6)1.2; m(1)4.9; bs(1)6.0; m(10)6.7–7.5 |

TABLE 1-continued

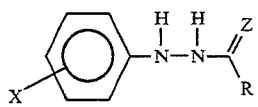

| COMPOUND | X | R | Z | NMR DATA FOR NOTES 1 (CDCL$_3$) |
|---|---|---|---|---|
| 51 | 3-C$_6$H$_5$ | OC$_2$H$_5$ | O | t(3)1.2; q(2)4.1; bs(1)5.9; m(10)6.7–7.6 |
| 52 | 2-CH$_3$O, 5-C$_6$H$_5$ | OCH(CH$_3$)$_2$ | O | m(9)1.2–1.6; m(2)4.0–4.3; m(1)4.8–5.2; bs(1)6.4; m(9)6.8–7.6 |
| 53 | 2-C$_6$H$_5$ | OC$_5$H$_{11}$ | O | m(9)0.8–1.7; m(2)3.9–4.2; bs(1)5.9 m(10)6.7–7.5 |
| 54 | 2-CH$_3$O, 5-C$_6$H$_5$ | OC$_5$H$_{11}$ | O | m(9)0.8–1.7; s(3)3.8; t(2)4.1; bs(1)6.3; m(9)6.7–7.5 |
| 55 | 2-CH$_3$O, 5-C$_6$H$_5$ | OC$_6$H$_{13}$ | O | m(11)0.8–1.7; s(3)3.9; t(2)4.1; bs(1)6.3; m(9)6.7–7.5 |
| 136 | 3-OCH$_2$C$_6$H$_5$ | C$_2$H$_5$ | O | t(3)1.2; q(2)4.1; s(2)5.0; bs(2)6.3; m(9)6.9–7.4 |
| 137 | 3-OCH$_2$C$_6$H$_5$ | CH(CH$_3$)$_2$ | O | d(6)1.3; m(1)5.0; s(2)5.1; bs(2)6.5; m(9)6.9–7.5 |
| 138 | 3-OC$_6$H$_5$ | CH(CH$_3$)$_2$ | O | s(9)1.4; bs(2)6.5; m(9)6.9–7.5 |
| 139 | 2-Br, 5-C$_6$H$_5$ | CH(CH$_3$)$_2$ | O | d(6)1.3; m(1)5.0; bs(1)6.3; m(8)6.9–7.5 |
| 140 | 3-OC$_6$H$_5$ | CH(CH$_3$)$_2$ | O | d(6)1.3; m(1)5.0; bs(2)6.6; m(9)6.9–7.5 |
| 143 | 3-OCH$_2$C$_6$H$_5$ | CH$_3$ | O | s(3)3.8; s(2)5.0; bs(2)6.5; m(9)7.0–7.5 |
| 144 | 3-OCH$_2$C$_6$H$_5$ | CH$_2$CH=CH$_2$ | O | d(2)4.5; m(3)5.1–6.0; bs(2)6.5; m(9)6.9–7.4 |
| 145 | 2-CH$_2$C$_6$H$_5$ | C$_3$H$_7$ | O | t(3)0.8; m(2)1.5; s(2)3.8; m(2)3.9; bs(2)6.4; m(9)6.9–7.3 |
| 146 | 2-CH$_2$C$_6$H$_5$ | CH$_2$CH=CH$_2$ | O | s(2)3.9; d(2)4.5; m(3)5.0–5.8; bs(2)6.6; m(9)6.8–7.3 |
| 147 | 3-OCH$_2$C$_6$H$_5$ | C(CH$_3$)$_3$ | O | s(9)1.4; s(2)5.0; bs(2)6.5; m(9)6.9–7.4 |
| 148 | 2-CH$_2$C$_6$H$_5$ | C(CH$_3$)$_3$ | O | s(9)1.4; s(2)3.9; bs(2)6.2; m(9)6.9–7.3 |
| 149 | 3-OC$_6$H$_5$ | CH(CH$_3$)C$_2$H$_5$ | O | t(3)0.8; d(3)1.2; m(2)1.5; m(1)4.8; bs(2)6.5; m(9)6.9–7.4 |
| 150 | 2-SCH$_3$, 5-C$_6$H$_5$ | CH(CH$_3$)$_2$ | O | d(6)1.2; s(3)2.4; m(1)4.9; bs(2)6.6; m(8)7.0–7.5 |
| 154 | 2-CH$_3$, 5-C$_6$H$_5$ | CH(CH$_3$)$_2$ | O | d(6)1.2; s(3)2.2; m(1)4.9; bs(1)5.8; bs(1)6.6; m(8)7.0–7.6 |
| 155 | 2-OCH$_3$, 5-OC$_6$H$_5$ | CH(CH$_3$)$_2$ | O | d(6)1.3; s(3)3.8; m(1)4.9; m(10)6.5–7.4 |

NOTES FOR TABLES 1-4B
(1) S = Singlet, d = doublet, t = triplet q = quartet, m = multiplet bs — broad singlet
(2) the number in parenthesis represents the number of protons
(3) CD CL$_3$ is deuterated chloroform

TABLE 2

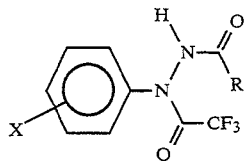

| COMPOUND | X | R | NMR DATA FOR TABLE 2 (CDCL$_3$) |
|---|---|---|---|
| 56 | 2-C$_6$H$_5$ | H | bs(1)5.8; m(9)6.8–7.5; bs(1)8.1 |
| 57 | 2-C$_6$H$_5$ | CH$_3$ | s(3)2.5; bs(1)6.0; m(9)6.8–7.5 |
| 58 | 2-C$_6$H$_5$ | OCH$_3$ | s(3)3.7; bs(1)5.7; m(9)7.3–7.6 |
| 59 | 2-C$_6$H$_5$ | OCH$_2$CH$_3$ | t(3)1.2; q(2)4.2; m(9)7.3–7.7; bs(1)9.7 |
| 60 | 2-C$_6$H$_5$ | C(CH$_3$)$_3$ | s(9)1.2; m(10)6.8–7.6 |
| 61 | 2-C$_6$H$_5$ | C$_5$H$_9$—C | m(8)1.7; m(10)6.8–7.6 |
| 62 | 2-C$_6$H$_5$ | OCH$_2$C$_6$H$_5$ | s(2)5.2; bs(1)6.9; m(9)7.3–7.6 |
| 63 | 2-C$_6$H$_5$ | CH$_3$ | s(3)2.0; m(9)7.3–7.9; bs(1)8.5 |
| 64 | 2-CH$_3$O, 5-C$_6$H$_5$ | H | s(3)3.9; b(1)5.5; m(8)7.0–7.7; bs(1)8.3 |
| 65 | 2-CH$_3$O, 5-C$_6$H$_5$ | CH$_3$ | s(3)2.0; s(3)3.8; bs(1)6.1; m(8)6.9–7.7 |
| 66 | 2-CH$_3$O, 5-C$_6$H$_5$ | OCH$_3$ | s(3)3.7; s(3)3.9; bs(1)4.2; m(8)7.3–7.8 |
| 67 | 2-CH$_3$O, 5-C$_6$H$_5$ | OCH$_2$CH$_3$ | t(3)1.1; s(3)3.8; q(2)4.1; m(9)7.2–7.8 |
| 68 | 2-CH$_3$O, 5-C$_6$H$_5$ | N(CH$_3$)$_2$ | s(6)3.0; s(3)3.9; m(9)7.0–7.9 |
| 69 | 2-CH$_3$O, 5-C$_6$H$_5$ | CH$_2$CH$_2$CH$_3$ | t(3)1.0; m(2)1.7; t(2)3.0; s(3)3.9; m(8)7.0–7.7; bs(1)8.2 |
| 70 | 2-CH$_3$O, 5-C$_6$H$_5$ | CH(CH$_3$)$_2$ | d(6)1.0; m(1)2.5; s(3)3.9; bs(1)5.4; m(8)7.0–7.9 |
| 71 | 2-CH$_3$O, 5-C$_6$H$_5$ | C(CH$_3$)$_3$ | s(9)1.2; s(3)3.9; m(8)7.0–7.9; bs(1)8.3 |
| 72 | 2-CH$_3$O, 5-C$_6$H$_5$ | OCH$_2$C$_6$H$_5$ | s(3)3.8; s(2)5.1; m(8)7.1–7.8; bs(1)9.5 |
| 73 | 2-CH$_3$O, 5-C$_6$H$_5$ | CH$_2$CH$_3$ | t(3)1.1; q(2); s(3)3.8; m(8)7.0–7.8; bs(1)8.1 |
| 74 | 2-CH$_3$O, 5-C$_6$H$_5$ | OCH$_2$CH$_2$CH$_3$ | m(7)0.8–1.7; s(3)3.9; t(2)4.1; m(9)7.0–7.8 |
| 75 | 2-CH$_3$O, 5-C$_6$H$_5$ | C(CH$_3$)=CH$_2$ | s(3)2.0; s(3)3.9; m(2)5.4–5.7; m(8)7.0–7.8; bs(1)8.3 |

TABLE 2-continued

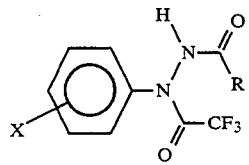

| COMPOUND | X | R | NMR DATA FOR TABLE 2 (CDCL$_3$) |
|---|---|---|---|
| 76 | 2-CH$_3$O, 5-C$_6$H$_5$ | CF$_3$ | s(3)3.9; m(9)7.1–7.8 |
| 77 | 2-CH$_3$O, 5-C$_6$H$_5$ | N(CH$_2$CH$_3$)$_2$ | t(6)1.2; m(4)3.3; s(3)3.8; m(9)7.0–8.0 |
| 79 | 2-CH$_3$O, 5-C$_6$H$_5$ | SCH$_2$CH$_3$ | t(3)1.2; q(2)2.8; s(3)3.9; m(9)7.2–7.8 |
| 78 | 2-CH$_3$O, 5-C$_6$H$_5$ | CO$_2$CH$_2$CH$_3$ | t(3)1.3; s(3)3.8; q(2)4.2; m(8)7.0–7.9; bs(1)9.5 |
| 80 | 2-CH$_3$O, 5-C$_6$H$_5$ | OCH$_2$CH=CH$_2$ | s(3)3.9; d(2)4.6; m(3)5.1–5.8; m(9)7.0–7.7 |
| 81 | 2-CH$_3$O, 5-C$_6$H$_5$ | OCH(CH$_3$)$_2$ | d(6)1.2; s(3)3.8; m(1)4.9; m(9)7.0–7.7 |
| 82 | 2-CH$_3$O, 5-C$_6$H$_5$ | CH$_2$C(CH$_3$)$_3$ | s(9)1.0; s(2)2.2; s(3)3.9; m(8)7.0–7.8; bs(1)8.6 |
| 83 | 2-CH$_3$O, 5-C$_6$H$_5$ | CF$_2$Cl | s(3)3.9; m(9)7.0–8.0 |
| 84 | 2-CH$_3$O, 5-C$_6$H$_5$ | 2-C$_4$H$_3$S | s(3)3.9; m(12)7.0–8.0 |
| 85 | 2-CH$_3$O, 5-C$_6$H$_5$ | 2-C$_4$H$_3$O | s(3)3.9; bs(1)6.5; m(11)7.0–8.0 |
| 86 | 2-CH$_3$O, 5-C$_6$H$_5$ | OCH$_2$CH$_3$ | m(6)1.3; m(4)4.2; m(9)7.0–7.8 |
| 87 | 2-CH$_3$O, 5-C$_6$H$_5$ | CH$_2$Cl | s(3)3.9; s(2)4.0; m(9)6.9–7.7 |
| 88 | 2-CH$_3$O, 5-C$_6$H$_5$ | CH$_2$C$_6$H$_5$ | s(2)3.7; s(3)3.8; m(14)6.8–7.9 |
| 89 | 2-CH$_3$O, 5-C$_6$H$_5$ | cyclohexyl | m(11)1.1–1.9; s(3)3.9; m(9)6.8–7.9 |
| 90 | 2-CH$_3$O, 5-C$_6$H$_5$ | OC$_3$H$_7$ | t(3)1.9; m(2)1.6; s(3)3.9; t(2)4.1; m(9)6.9–7.8 |
| 91 | 2-CH$_3$O, 5-C$_6$H$_5$ | CH$_2$OCH$_3$ | s(3)3.4; s(3)3.9; s(2)4.0; m(9)6.9–7.9 |
| 92 | 2-CH$_3$O, 5-C$_6$H$_5$ | OCH$_2$CH(CH$_3$)$_2$ | d(6)0.9; m(1)1.8; s(3)3.9; d(2)4.0; m(9)6.9–7.8 |
| 93 | 2-C$_6$H$_5$ | OCH$_2$CH(CH$_3$) | d(6)0.9; m(1)1.8; d(2)3.9; bs(1)6.1; m(9)7.2–7.7 |
| 94 | 2-CH$_3$O, 5-C$_6$H$_5$ | CH$_3$ | t(3)1.5; s(3)2.0; s(3)4.1; m(8)6.9–7.8; bs(1)8.3 |
| 95 | 2-CH$_3$O, 5-C$_6$H$_5$ | OCH(CH$_3$)$_2$ | d(6)1.3; m(1)5.0; m(9)7.3–7.8; bs(1)10.7 |
| 96 | 2-CH$_3$O, 5-C$_6$H$_5$ | OCH$_2$CH$_2$Cl | t(2)3.7; s(3)3.9; t(2)4.3; m(9)6.9–7.8 |
| 97 | 2-CH$_3$O, 5-C$_6$H$_5$ | OC$_6$H$_5$ | s(3)3.9; m(14)6.8–7.9 |
| 98 | 2-CH$_3$O, 5-C$_6$H$_5$ | OC$_4$H$_9$ | m(7)0.8–1.7; m(2)4.1; bs(1)6.2 m(9)7.2–7.6 |
| 99 | 2-C$_6$H$_5$ | OC$_3$H$_7$ | m(5)0.8–1.6; m(2)4.0; bs(1)6.2; m(9)7.0–7.7 |
| 100 | 2-CH$_3$O, 5-C$_6$H$_5$ | OCH=CH$_2$ | s(3)3.9; m(2)4.5–5.0; s(1)6.2; m(10)6.8–7.8 |
| 101 | 2-CH$_3$O, 5-C$_6$H$_5$ | OC$_5$H$_{11}$ | m(9)0.8–1.6; s(3)3.8; m(2)4.1–6.2; m(9)6.8–7.7 |
| 102 | 2-CH$_3$O, 5-C$_6$H$_5$ | OC$_6$H$_{13}$ | m(11)0.8–1.6; s(3)3.8; m(2)4.1; m(9) 6.8–7.7 |

NOTES FOR TABLES 1-4B
(1) S = Singlet, d = doublet, t = triplet q = quartet, m = multiplet bs — broad singlet
(2) the number in parenthesis represents the number of protons
(3) CD CL$_3$ is deuterated chloroform

TABLE 3

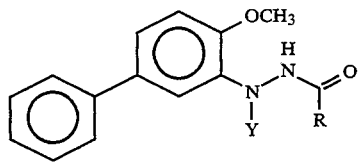

| COMPOUND | Y | R | NMR DATA FOR TABLE 3 (CDCL$_3$) |
|---|---|---|---|
| 103 | COCH$_3$ | CF$_3$ | s(3)2.0; s(3)3.9; m(9)7.2–7.8 |
| 104 | COCH$_2$Cl | CH$_3$ | 5(3)2.3; s(3)3.9; s(2)4.5; m(9)7.2–7.8 |
| 105 | COCF$_2$CF$_3$ | CH$_3$ | s(3)2.5; s(3)3.9; m(9)7.0–7.6 |
| 106 | COCF$_2$CF$_3$ | OCH$_3$ | s(3)3.4; s(3)3.9; s(2)4.0; m(8)7.0–8.0; bs(1)8.8 |
| 107 | COCH$_2$CH$_3$ | CF$_3$ | t(3)1.0; m(2)2.2; s(3)3.9; m(8)7.0–7.9; bs(1)9.0 |
| 108 | CO$_2$CH$_2$CH$_3$ | CF$_3$ | t(3)1.2; s(3)3.9; q(2)4.2; m(9)7.0–7.8 |
| 109 | CONHCH$_3$ | OCH$_2$CH$_3$ | t(3)1.2; d(2)2.9; s(3)3.9; m(10)7.0–7.8 |
| 110 | COCH$_3$ | CH$_3$ | s(3)2.0; s(3)3.4; s(3)3.9; m(8)6.9–7.7; bs(1)9.8 |
| 111 | COCF$_2$Cl | CH$_3$ | s(3)2.0; s(3)3.9; m(9)6.7–7.8 |
| 112 | COCH$_3$ | CF$_2$CF$_3$ | s(3)2.0; s(3)3.9; m(8)6.9–7.8; bs(1)8.9 |
| 113 | COCH$_3$ | CF$_2$Cl | s(3)2.0; s(3)3.9; m(8)6.9–7.8; bs(1)8.7 |
| 114 | COCF$_2$CF$_3$ | CF$_3$ | s(3)3.9; m(9)6.9–7.9 |

TABLE 3-continued

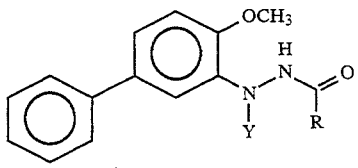

| COMPOUND | Y | R | NMR DATA FOR TABLE 3 (CDCL₃) |
|---|---|---|---|
| 115 | COCF₂Cl | CF₃ | s(3)3.9; m(9)6.9–7.8 |
| 116 | PO(OC₂H₅)₂ | CF₃ | t(6)1.3; s(3)3.8; q(4)4.2; m(9)6.8–7.5 |
| 117 | COCH₂Cl | CF₃ | s(3)3.9; s(2)4.1; m(9)6.8–7.8 |
| 118 | COCF₂CF₃ | OCH(CH₃)₂ | d(6)1.2; s(3)3.9; m(1)4.9; m(9)6.9–7.8 |
| 119 | COCF₂Cl | OCH(CH₃)₂ | d(6)1.2; s(3)3.8; m(1)4.9; m(9)6.9–7.8 |
| 120 | CONHCH₃ | OCH(CH₃)₂ | d(6)1.2; d(3)2.8; s(3)3.8; m(1)4.9; m(1)5.3; m(9)6.9–7.8 |
| 121 | COCCl₃ | CF₃ | s(3)3.9; m(9)6.8–7.7 |
| 122 | CON(CH₃)₂ | OCH(CH₃)₂ | d(6)1.4; s(6)2.7; s(3)3.9; m(1)5.0; m(9)6.8–7.8 |
| 123 | COCF₂CF₃ | CF₂Cl | d(3)3.8; m(8)6.8–7.8; bs(1)8.5 |
| 124 | COCF₂CF₃ | CF₃ | d(3)3.8; m(8)6.8–7.7; bs(1)8.6 |
| 125 | SO₂CF₃ | CF₃ | d(3)3.8; m(9)6.8–7.8 |
| 126 | CO₂CH₃ | CF₃ | s(3)3.8; s(3)3.9; m(9)6.8–7.8 |
| 127 | COCF₂CF₃ | OCH₂C₆H₅ | s(3)3.8; s(2)5.0; m(14)6.8–7.8 |
| 128 | CONHCH₃ | CF₃ | bs(3)2.7; s(3)3.8; bs(1)5.5; m(8)6.8–7.8; s(1)9.2 |
| 129 | COCH₃ | OCH₃ | s(3)3.7; s(3)3.8; m(9)6.8–7.8 |
| 130 | CONHC₂H₅ | CF₃ | t(3)1.1; m(2)3.1; s(3)3.8; bs(1)5.8; m(9)6.8–7.8 |
| 131 | CONHC₂H₅ | OCH(CH₃)₂ | m(9)1.2; m(2)3.2; s(3)3.8; m(1)4.9; m(9)6.8–7.8 |
| 132 | COCH₃ | OCH—CH₂ | s(3)2.0; s(3)3.8; m(2)4.4–4.9; m(1)6.5; m(9)6.8–7.8 |
| 133 | PO(OCH₂H₅)₂ | OCH(CH₃)₂ | m(12)1.3; s(3)3.9; m(4)4.1; m(1)5.0; m(9)6.8–7.7 |
| 134 | PO(OC₂H₅)₂ | OCH₂CH₃ | m(9)1.2; s(3)3.8; q(6)4.1; m(9)6.8–7.7 |

NOTES FOR TABLES 1–4B
(1) S = Singlet, d = doublet, t = triplet q = quartet, m = multiplet bs — broad singlet
(2) the number in parenthesis represents the number of protons
(3) CD CL₃ is deuterated chloroform

TABLE 4

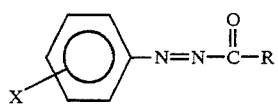

| COMPOUND | X | R | NMR DATA FOR TABLE 4 (CDCL₃) |
|---|---|---|---|
| 135 | 2-CH₃O, 5-C₆H₅ | OCH(CH₃)₂ | d(6)1.5; s(3)4.0; m(1)5.2; m(8)7.0–7.9 |
| 156 | 3-OC₆H₅ | OC(CH₃)₃ | s(9)1.6; m(9)7.0–7.5 |
| 158 | 3-OCH₂C₆H₅ | OC₂H₅ | t(3)1.4; q(2)4.4; s(2)5.0; m(9)7.1–7.5 |
| 159 | 2-CH₃, 5-C₆H₅ | OCH(CH₃)₂ | d(6)1.5; s(3)2.7; m(1)5.2; m(8)7.2–7.8 |
| 160 | 2-OCH₃, 5-OC₆H₅ | OCH(CH₃)₂ | d(6)1.4; s(3)4.0; m(1)5.2; m(8)6.9–7.4 |
| 161 | 2-Br, 5-C₆H₅ | OCH(CH₃)₂ | d(6)1.5; m(1)5.3; m(8)7.0–7.7 |

TABLE 4A

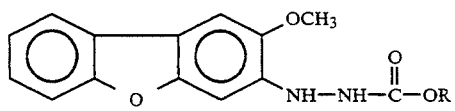

| COMPOUND | R | NMR DATA FOR TABLE 4A (CDCL₃) |
|---|---|---|
| 141 | CH(CH₃)₂ | d(6)1.2; s(3)3.9; m(1)5.0; bs(2)6.5; m(6)7.0–7.6 |
| 142 | C(CH₃)₃ | s(9)1.5; s(3)4.0; bs(2)6.5; m(6)7.1–7.6 |
| 151 | CH₂CH—CH₂ | s(3)4.0; d(2)4.7; m(3)5.1–5.8; bs(2)6.5; m(6)7.1–7.6 |
| 152 | CH₃ | s(3)3.8; s(3)4.0; bs(2)6.5; m(6)7.0–7.6 |
| 153 | C₃H₇ | t(3)1.0; m(2)1.6; s(3)4.0; m(2)4.2; bs(2)6.6; m(6)7.1–7.6 |

TABLE 4B

Structure: benzofuran-O-phenyl(OCH₃)(N=N-C(=O)-OR)

| COMPOUND | R | NMR DATA FOR TABLE 4B (CDCL₃) |
|---|---|---|
| 157 | CH(CH₃)₂ | d(6)1.4; s(3)4.1; m(6)7.1–7.7 |

EXAMPLE 10

Preparation of Formulations

The remaining examples relate to the pesticidal use of the compounds of this invention. In all these examples a stock solution for the compounds were prepared at 3000 ppm by dissolving 0.3 gram of the compound to be tested in 10 ml of acetone and adding 90 ml of distilled water plus for drops of ethoxylated sorbitan monolaurate, or a simliar suitable wetting agent. For each example that follows, this stock solution was used and the specified dilutions made. All the tests discussed below, which involved treatment with compounds of this invention, were always repeated with controls, in which the active compound was not provided, to permit a comparison upon which the percent control was calculated.

EXAMPLE 11

Mite Adulticide and Mite Ovicide/Larvicide Tests

One day before treatment, a "figure 8" configuration of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when they were removed. Plants were sprayed to run off with a 1000 ppm solution diluted from the 3000 ppm stock solution.

One day following treatment, groups of approximately 25 adult mites were transferred into the adulticide rings. Five days later these rings were examined for live mites remaining on the leaves. The percent control was estimated based on the number of mites surviving on the check plants.

Nine days following treatment the ovicide/larvicide rings were examined for hatched eggs and living immature mites. The percent control was estimated based on the number of eggs hatching and immature mites surviving on the check plants. When the treatment effect was to eggs, control was designated as ovicidal (O); when the treatment effect was to immatures, control was designated as larvicidal (L).

Results of the mite adulticide (MI) and ovicide/larvicide (MIOLV) tests are presented in Table 5.

TABLE 5

| COMPOUND NO. | MI | MIOVL |
|---|---|---|
| 1 | 50 | 80(L) |
| 2 | 100 | 100 |
| 3 | 100 | 100(L) |
| 4 | 100 | 100(L) |
| 5 | 30 | 80(L) |
| 6 | 100 | 100(L) |
| 7 | 100 | 100(O) |
| 8 | 70 | 0 |
| 9 | 70 | 0 |
| 10 | 100 | 100(O/L) |
| 11 | 100 | 100(O/L) |
| 12 | 95 | 90(L) |
| 13 | 70 | 70(L) |
| 14 | 100 | 100(L) |
| 15 | 100 | 100(L) |
| 16 | 100 | 100(L) |
| 17 | 70 | 0 |
| 18 | 98 | 100(L) |
| 19 | 100 | 100(O) |
| 20 | 100 | 100(O) |
| 21 | 100 | 100(O) |
| 22 | 100 | 20(L) |
| 23 | 70 | 0 |
| 24 | 100 | 70(L) |
| 25 | 100 | 100(O) |
| 26 | 100 | 100(O) |
| 27 | 99 | 50(L) |
| 28 | 100 | 100(L) |
| 29 | 80 | 80(L) |
| 30 | 50 | 50(L) |
| 39 | 100 | 100(L) |
| 40 | 50 | 0 |
| 41 | 80 | 50(L) |
| 42 | 100 | 100(O) |
| 43 | 100 | 100(O) |
| 44 | 50 | 30(L) |
| 45 | 70 | 50(L) |
| 46 | 100 | 30(L) |
| 47 | 100 | 100(L) |
| 49 | 100 | 100(O) |
| 50 | 100 | 100(O) |
| 51 | 100 | 100(O) |
| 52 | 100 | 100(O) |
| 53 | 100 | 100(L) |
| 54 | 100 | 100(O) |
| 55 | 100 | 100(O) |
| 56 | 70 | 0 |
| 57 | 90 | 95(L) |
| 58 | 100 | 30 |
| 59 | 100 | 0 |
| 60 | 100 | 100(L) |
| 62 | 98 | 50(L) |
| 63 | 100 | 70(L) |
| 64 | 100 | 100(L) |
| 65 | 100 | 100(L) |
| 66 | 70 | 50(L) |
| 67 | 90 | 95(L) |
| 68 | 100 | 100(L) |
| 69 | 100 | 100(L) |
| 70 | 100 | 100(L) |
| 72 | 0 | 50(L) |
| 73 | 100 | 100(L) |
| 74 | 99 | 30(L) |
| 75 | 100 | 100(L) |
| 76 | 100 | 100(L) |
| 77 | 100 | 100(L) |
| 78 | 100 | 100(L) |
| 79 | 70 | 70(L) |
| 80 | 100 | 70(L) |
| 81 | 99 | 90(L) |
| 82 | 95 | 30(L) |
| 83 | 100 | 100(L) |
| 84 | 100 | 100(L) |
| 85 | 100 | 100(L) |
| 86 | 100 | 100(L) |
| 93 | 100 | 80(1) |
| 94 | 100 | 100(L) |
| 95 | 100 | 100(L) |
| 96 | 100 | 100(L) |
| 97 | 70 | 30(L) |
| 98 | 100 | 100(L) |
| 99 | 100 | 100(L) |
| 101 | 70 | 80(L) |
| 102 | 70 | 0 |

TABLE 5-continued

| COMPOUND NO. | MI | MIOVL |
|---|---|---|
| 105 | 95 | 0 |
| 107 | 100 | 50(L) |
| 108 | 100 | 100(O) |
| 109 | 100 | 100(O) |
| 112 | 60 | 0 |
| 114 | 100 | 100(O) |
| 115 | 100 | 100(L) |
| 116 | 100 | 100(L) |
| 117 | 100 | 100(L) |
| 118 | 100 | 100(L) |
| 119 | 100 | 100(L) |
| 120 | 100 | 100(L) |
| 121 | 100 | 100(L) |
| 122 | 100 | 100(O) |
| 124 | 100 | 100(L) |
| 125 | 80 | 30(L) |
| 126 | 100 | 100(L) |
| 128 | 100 | 100(L) |
| 130 | 100 | 50(L) |
| 131 | 100 | 100(L) |
| 133 | 100 | 100(O) |
| 135 | 100 | 100(O) |
| 136 | 98 | 100(L) |
| 137 | 100 | 100(L) |
| 138 | 100 | 98(L) |
| 139 | 100 | 100(L) |
| 140 | 100 | 100(L) |
| 141 | 70 | 100(L) |
| 142 | 50 | 80(L) |
| 143 | 70 | 30(O) |
| 144 | 30 | 0 |
| 145 | 100 | 90(L) |
| 146 | 70 | 50(L) |
| 147 | 100 | 100(L) |
| 148 | 70 | 30(L) |
| 149 | 30 | 0 |
| 150 | 80 | 0 |
| 151 | 0 | 0 |
| 152 | 0 | 0 |
| 153 | 100 | 90(L) |
| 154 | 100 | 100(L) |
| 155 | 0 | 0 |
| 156 | 98 | 0 |
| 157 | 30 | 80(L) |
| 158 | 100 | 98(O) |
| 159 | 100 | 100(O) |
| 160 | 100 | 20(O) |
| 161 | 100 | 100(O) |

NOTES:
MI = MITE ADULTICIDE
MIOVL = MITE OVICIDE/LARVICIDE

EXAMPLE 12

European Red Mite Test

Orchard apple trees with infestations of European red mite (*Panonychus ulmi*) were sprayed with aqueous solutions of emulsifiable concentrates of individual compounds. Greater than 75 percent control with an application rate of 150 ppm ai was achieved by compound numbers 103, 10, 11, 19, 20, 25, 26, and 82.

EXAMPLE 13

Nematode Test

The stock solution of 3000 ppm was diluted to 1000 ppm. For each compound, 25 ml was drenched onto 500 grams of soil infested with root knot nematode (*Meloidogyne incognita*) eggs in a pot, for a soil concentration of 50 ppm sc.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table 6.

EXAMPLE 14

Rice Planthopper Foliar Test

The stock solution of 3000 ppm was diluted to 1000 ppm. One pot containing approximately 20 Mars variety rice seedlings was treated with each formulation by spraying with a spray atomizer. One day after treatment plants were covered with a tubular cage and twenty adult rice delphacids, *Sogatodes oryzicola*, were transferred into each cage. Five days after transferring, counts were made of the surviving planthoppers in each pot and percent control was estimated.

The results of the testing of rice planthoppers (RPH) are given in Table 6.

EXAMPLE 15

Tobacco Budworm Test

The stock solution of 3000 ppm was used for this test. For each compound, 0.2 ml was piperted onto the surface of each of 5 diet cells, allowed to spread over the surfaces and air dried for two hours. Then a second istar *Heliothis virescens* larva was introduced into each cell. After 14 days, the number of living larvae was determined for each treatment and percent control, corrected by Abbott's formula, was calculated.

The results of the testing of tobacco budworms (TB) are given in Table 6.

EXAMPLE 16

Southern Corn Rootworm Test

The stock solution of 3000 ppm was diluted to 100 ppm. For each compound, 2.5 ml was pipetted onto a filter paper (Whatman #3) at the bottom of a 100 mm petri dish. Two corn seedlings were soaked in the 100 ppm solution for 1 hour and transferred to the petri dish. After 24 hours, each dish was loaded with 5 second instar larvae of *Diabrotica undecimpunctata*. After five days, the number of live larvae were noted and the percent control, corrected by Abbott's formula (see J. Economic Entomology, 18, 265–267 (1925)) was calculated.

The results appear in Table 6.

TABLE 6

| COMPOUND NO. | PERCENT CONTROL | | | |
|---|---|---|---|---|
| | NE | RPH | TB | SCR |
| 1 | 0 | 30 | 100 | 0 |
| 2 | 30 | 100 | 79 | 75 |
| 3 | 0 | 100 | 58 | 50 |
| 4 | 70 | 100 | 100 | 100 |
| 5 | 0 | 0 | 100 | 0 |
| 6 | 0 | 100 | 100 | 0 |
| 7 | 0 | 100 | 100 | 100 |
| 8 | 50 | PT | 0 | 0 |
| 9 | 85 | 0 | 0 | 0 |
| 10 | 0 | 50 | 20 | 0 |
| 11 | 0 | 10 | 100 | 0 |
| 12 | 50 | 0 | 20 | 0 |
| 13 | 0 | 5 | 100 | 0 |
| 14 | 70 | 0 | 0 | 0 |
| 17 | 70 | 0 | 0 | 0 |
| 18 | 0 | 0 | 80 | 0 |
| 19 | 70 | 60 | 0 | 14 |
| 20 | 0 | 0 | 80 | 0 |
| 23 | 95 | 0 | 75 | 0 |
| 24 | 0 | 80 | 0 | 0 |

TABLE 6-continued

| COMPOUND NO. | PERCENT CONTROL | | | |
|---|---|---|---|---|
| | NE | RPH | TB | SCR |
| 25 | 30 | 0 | 56 | 0 |
| 26 | 20 | 0 | 100 | 0 |
| 27 | 0 | 0 | 56 | 0 |
| 28 | 70 | 0 | 40 | 6 |
| 31 | 50 | 55 | 100 | 15 |
| 33 | 0 | 20 | 100 | 0 |
| 34 | 50 | 15 | 0 | 0 |
| 35 | 100 | 20 | 0 | 0 |
| 36 | 50 | 0 | 0 | 20 |
| 37 | PT | 25 | 80 | 17 |
| 38 | 0 | 0 | 80 | 0 |
| 42 | 0 | 100 | 100 | 100 |
| 43 | 0 | 100 | 100 | 80 |
| 45 | 0 | 0 | 100 | 0 |
| 47 | 80 | 50 | 0 | 20 |
| 48 | 50 | 25 | 0 | 0 |
| 49 | 0 | 80 | 0 | 0 |
| 50 | 30 | 100 | 0 | 100 |
| 51 | 30 | 100 | 100 | 0 |
| 53 | 0 | 100 | 100 | 0 |
| 54 | 0 | 95 | 80 | 0 |
| 55 | 0 | 70 | 40 | 0 |
| 57 | 0 | 35 | 100 | 37 |
| 58 | 0 | 25 | 100 | 0 |
| 59 | 50 | 20 | 100 | 75 |
| 60 | 0 | 40 | 60 | — |
| 62 | 0 | 0 | 100 | 0 |
| 64 | 70 | 25 | 0 | 21 |
| 65 | 60 | 0 | 0 | 0 |
| 67 | 0 | 10 | 100 | 0 |
| 74 | 0 | 0 | 80 | 0 |
| 78 | 95 | 0 | 0 | 14 |
| 80 | 0 | 0 | 78 | 0 |
| 81 | 0 | 50 | 78 | 0 |
| 83 | 30 | 50 | 73 | 16 |
| 84 | 0 | 50 | 20 | 6 |
| 87 | 50 | 0 | 0 | 0 |
| 88 | 50 | 0 | 100 | 0 |
| 89 | 0 | 0 | 60 | 33 |
| 90 | 0 | 0 | 100 | 0 |
| 91 | 0 | 70 | 80 | 0 |
| 92 | 0 | 0 | 75 | 0 |
| 95 | 0 | 25 | 100 | 100 |
| 96 | 30 | 0 | 50 | 20 |
| 99 | 0 | 80 | 0 | 100 |
| 100 | 70 | 60 | 0 | 0 |
| 102 | 70 | 0 | 0 | 0 |
| 103 | 0 | 0 | 100 | 0 |
| 103 | 0 | 0 | 100 | 0 |
| 105 | 0 | 0 | 100 | 0 |
| 106 | 30 | 55 | 0 | 0 |
| 108 | 70 | 0 | 0 | 0 |
| 110 | 0 | 30 | 100 | 0 |
| 111 | 0 | 0 | 100 | 20 |
| 112 | 50 | 0 | 0 | 0 |
| 113 | 0 | 0 | 100 | 6 |
| 115 | 70 | 50 | 16 | 0 |
| 116 | 60 | 0 | 0 | 60 |
| 117 | 50 | 0 | 55 | 33 |
| 119 | 0 | 40 | 78 | 0 |
| 121 | 50 | 40 | 0 | 0 |
| 125 | 98 | 25 | 0 | 0 |
| 127 | 50 | 50 | 0 | 0 |
| 128 | 70 | 30 | 0 | 0 |
| 129 | 50 | 25 | 0 | 0 |
| 130 | 70 | 15 | 0 | 16 |
| 131 | 70 | 25 | 0 | 16 |
| 132 | 70 | 50 | 0 | 0 |
| 133 | 0 | 55 | 60 | 0 |
| 134 | 70 | 60 | 0 | 0 |
| 135 | — | 55 | — | — |
| 136 | 100 | 30 | 20 | 0 |
| 137 | 100 | 25 | 0 | 100 |
| 138 | 0 | 90 | 0 | 0 |
| 139 | 0 | 98 | 0 | 40 |
| 140 | 0 | 0 | 0 | 0 |
| 141 | 100 | 0 | 60 | 0 |
| 142 | 0 | 0 | 60 | 0 |
| 143 | PT | 0 | 20 | 20 |
| 144 | 0 | 0 | 0 | 80 |
| 145 | 0 | 0 | 0 | 80 |
| 146 | 0 | PT | 0 | 20 |
| 147 | 0 | 0 | 0 | 100 |
| 148 | 0 | 0 | 0 | 100 |
| 149 | 50 | 0 | 0 | 60 |
| 150 | 0 | 0 | 36 | 0 |
| 151 | 0 | 0 | 60 | 20 |
| 152 | 0 | 0 | 60 | 0 |
| 153 | 50 | 0 | 37 | 0 |
| 154 | 0 | 80 | 58 | 0 |
| 155 | — | 0 | 75 | 0 |
| 156 | 0 | 0 | 0 | 0 |
| 157 | 100 | 0 | 40 | 0 |
| 158 | — | — | — | — |
| 159 | 0 | 100 | 58 | 0 |
| 160 | — | 0 | 0 | 0 |
| 161 | — | 100 | 100 | 60 |

NOTES:
NE = NEMATODE
RPH = RICE PLANT HOPPER
TB = TOBACCO BUDWORK
SCR = SOUTHERN CORN ROOTWORK
PT = PHYTOTOXIC - PLANT DIED, NO SCORE APPLICABLE

What is claimed is:

1. A compound having the structural formula:

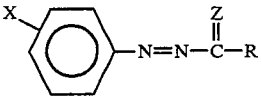 (II)

wherein

X is a) phenyl; lower phenylalkoxy; phenoxy; or benzyl; the phenyl ring of each substituent being optionally substituted with one or more of halogen, nitro, lower alkyl, lower alkoxy, lower haloalkyl or dialkylamino; or b) one substituent from group a) and one or more substituents selected from $C_1$–$C_4$ alkoxy; halogen; lower alkyl; and lower alkylthio;

R is H, $C_1$–$C_6$ alkyl, $C_1$–$C_6$ alkoxy, $C_1$–$C_4$ haloalkyl, or $C_3$–$C_6$ cycloalkyl; and Z is O.

2. A compound in accordance with claim 1 wherein X is phenyl or alkoxy; and

R is $CF_3$, $C_1$–$C_4$ alkyl; $C_1$–$C_4$ alkoxy, or $C_3$–$C_6$ cycloalkyl.

3. A pesticidal composition comprising
A) a pesticidally effective amount of a compound in accordance with claim 1; and
B) an acceptable carrier.

4. A process for controlling undesirable pests which comprises applying to a locus to be protected a pesticidally effective amount of a compound in accordance with claim 1.

* * * * *